United States Patent
Park et al.

(10) Patent No.: US 12,145,129 B2
(45) Date of Patent: Nov. 19, 2024

(54) SUPERABSORBENT POLYMER COMPOSITION AND METHOD FOR PREPARING THE SAME

(71) Applicant: LG Chem, Ltd., Seoul (KR)

(72) Inventors: Bohee Park, Daejeon (KR); Jun Kyu Kim, Daejeon (KR); Dong Hyun Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 879 days.

(21) Appl. No.: 17/270,338

(22) PCT Filed: Oct. 10, 2019

(86) PCT No.: PCT/KR2019/013302
§ 371 (c)(1),
(2) Date: Feb. 22, 2021

(87) PCT Pub. No.: WO2020/122390
PCT Pub. Date: Jun. 18, 2020

(65) Prior Publication Data
US 2021/0322953 A1 Oct. 21, 2021

(30) Foreign Application Priority Data

Dec. 12, 2018 (KR) .................. 10-2018-0160287
Oct. 8, 2019 (KR) .................. 10-2019-0124302

(51) Int. Cl.
| | | |
|---|---|---|
| B01J 20/26 | (2006.01) | |
| A61L 15/60 | (2006.01) | |
| B01J 20/28 | (2006.01) | |
| B01J 20/30 | (2006.01) | |
| B01J 20/32 | (2006.01) | |
| B29B 9/02 | (2006.01) | |
| B29B 9/12 | (2006.01) | |
| B29B 9/16 | (2006.01) | |
| B29B 13/06 | (2006.01) | |
| B29B 13/10 | (2006.01) | |

(52) U.S. Cl.
CPC ....... *B01J 20/267* (2013.01); *B01J 20/28004* (2013.01); *B01J 20/28021* (2013.01); *B01J 20/3021* (2013.01); *B01J 20/3085* (2013.01); *B01J 20/321* (2013.01); *B01J 20/3219* (2013.01); *B01J 20/3278* (2013.01); *B01J 20/3293* (2013.01); *B29B 9/02* (2013.01); *B29B 9/12* (2013.01); *B29B 9/16* (2013.01); *B29B 13/065* (2013.01); *B29B 13/10* (2013.01); *A61L 15/60* (2013.01); *B29B 2009/125* (2013.01); *B29B 2009/163* (2013.01)

(58) Field of Classification Search
None
See application file for complete search history.

(56) References Cited

U.S. PATENT DOCUMENTS

| | | |
|---|---|---|
| 4,497,930 A | 2/1985 | Yamasaki et al. |
| 4,666,983 A | 5/1987 | Tsubakimoto et al. |
| 4,758,617 A | 7/1988 | Tanioku et al. |
| 4,806,578 A | 2/1989 | Kobayashi et al. |
| 5,597,873 A | 1/1997 | Chambers et al. |
| 5,760,080 A | 6/1998 | Wada et al. |
| 6,054,541 A | 4/2000 | Wada et al. |
| 6,180,724 B1 | 1/2001 | Wada et al. |
| 6,265,488 B1 | 7/2001 | Fujino et al. |
| 6,417,425 B1 | 7/2002 | Whitmore et al. |
| 6,605,673 B1 | 8/2003 | Mertens et al. |
| RE38,444 E | 2/2004 | Wada et al. |
| 9,624,328 B2 | 4/2017 | Won et al. |
| 10,144,809 B2 | 12/2018 | Lee et al. |
| 2003/0045847 A1 | 3/2003 | Whitmore et al. |
| 2004/0214946 A1 | 10/2004 | Smith et al. |
| 2015/0315321 A1 | 11/2015 | Won et al. |
| 2015/0352520 A1* | 12/2015 | Suarez-Hernandez .............. B01J 20/3014 502/402 |

(Continued)

FOREIGN PATENT DOCUMENTS

| | | |
|---|---|---|
| CN | 105754754 A | 7/2016 |
| EP | 0618005 A2 | 10/1994 |

(Continued)

OTHER PUBLICATIONS

US 10,066,061 B2, 09/2018, Lee et al. (withdrawn)
Translation of WO2014/021388 (Year: 2014).*
"UV Coatings: Basics, Recent Developments and New Application", (Elsevier 2007), Dec. 21, 2006, p. 115.
International Search Report for application No. PCT/KR2019/013302 dated Feb. 10, 2020, 2 pages.
Odian, George, Principles of Polymerization, Second Edition (Wiley, 1981), Odian, p. 203.
Extended European Search Report including Written Opinion for Application No. 19896240.9 dated Nov. 18, 2021, pp. 1-12.
Denacol Catalog, Epoxy Compound, Nagase Kasei Kogyo Co., Ltd. (1998) 33 pgs. [Summary of English translation is provided].
Third Party Observation for International Application No. PCT/KR2019/013302, dated Apr. 7, 2021, 13 pages.

*Primary Examiner* — Tanisha Diggs
(74) *Attorney, Agent, or Firm* — Lerner David LLP

(57) ABSTRACT

The invention relates to superabsorbent polymer that not only has excellent basic absorption performance, but also exhibits more improved permeability under pressure, and thus, can improve rewet property and leak inhibition property of hygienic products such as a diaper, and the like, and a method for preparing the same. The superabsorbent polymer comprises base resin powder comprising first crosslinked polymer of water soluble ethylenically unsaturated monomers having acid groups of which at least a part are neutralized; and a surface crosslink layer on the base resin powder, comprising second crosslinked polymer formed by additional crosslinking of the first crosslinked polymer by a surface crosslinking agent, wherein the surface crosslinking agent comprises a polymer type first surface crosslinking agent having number average molecular weight of 300 or more, and having plural hydroxy groups or epoxy groups.

12 Claims, No Drawings

(56) References Cited

U.S. PATENT DOCUMENTS

| | | |
|---|---|---|
| 2017/0198105 A1 | 7/2017 | Lee et al. |
| 2018/0050321 A1 | 2/2018 | Lee et al. |
| 2018/0179329 A1 | 6/2018 | Kim et al. |
| 2019/0099739 A1 | 4/2019 | Lee et al. |
| 2019/0276609 A1 | 9/2019 | Lee et al. |
| 2020/0009529 A1 | 1/2020 | Nam et al. |
| 2020/0010624 A1 | 1/2020 | Nam et al. |

FOREIGN PATENT DOCUMENTS

| | | |
|---|---|---|
| EP | 0937736 A2 | 8/1999 |
| EP | 3249002 A1 | 11/2017 |
| EP | 3406653 A1 | 11/2018 |
| EP | 3424988 A1 | 1/2019 |
| EP | 3527611 A1 | 8/2019 |
| EP | 3705510 A1 | 9/2020 |
| EP | 3730539 A1 | 10/2020 |
| GB | 2126591 A | 3/1984 |
| GB | 2179663 A | 3/1987 |
| JP | H08057311 A | 3/1996 |
| JP | H10500712 A | 1/1998 |
| JP | H10244151 A | 9/1998 |
| JP | H11310644 A | 11/1999 |
| JP | 2002284892 A | 10/2002 |
| JP | 2006526691 A | 11/2006 |
| JP | 2007314794 A | 12/2007 |
| JP | 2008120948 A | 5/2008 |
| JP | 2011213936 A | 10/2011 |
| JP | 4921672 B2 | 4/2012 |
| KR | 20010104366 A | 11/2001 |
| KR | 20140130034 A | 11/2014 |
| KR | 20160084701 A | 7/2016 |
| KR | 20160117180 A | 10/2016 |
| KR | 20170033634 A | 3/2017 |
| KR | 20170100395 A | 9/2017 |
| KR | 101797391 B1 | 11/2017 |
| KR | 20180040404 A | 4/2018 |
| KR | 20180067940 A | 6/2018 |
| KR | 20180092661 A | 8/2018 |
| WO | 2014021388 A1 | 2/2014 |
| WO | 2018110760 A1 | 6/2018 |
| WO | 2018117390 A1 | 6/2018 |

* cited by examiner

SUPERABSORBENT POLYMER COMPOSITION AND METHOD FOR PREPARING THE SAME

CROSS-REFERENCE TO RELATED APPLICATIONS

The present application is a national phase entry under 35 U.S.C. § 371 of International Application No. PCT/KR2019/013302, filed on Oct. 10, 2019, which claims priority to Korean Patent Application No. 10-2018-0160287 filed on Dec. 12, 2018 and Korean Patent Application No. 10-2019-0124302 filed on Oct. 8, 2019, the disclosures of which are herein incorporated by reference in their entirety.

TECHNICAL FIELD

The invention relates to superabsorbent polymer that not only has excellent basic absorption performance, but also exhibits more improved permeability under pressure, and thus, can improve rewet property and leakage inhibition property of hygienic products such as a diaper, and the like, and a method for preparing the same.

BACKGROUND OF ART

Super absorbent polymer (SAP) is synthetic polymer material that can absorb moisture of 500 to 1000 times of self-weight, and is also named differently as super absorbency material (SAM), absorbent gel material (AGM), etc. according to developing companies. The superabsorbent polymer began to be commercialized as sanitary items, and currently, it is being widely used as hygienic goods such as a disposable diaper and the like, water-holding material for soil, water stop material for civil engineering and architecture, sheets for raising seedling, freshness preservatives in the field of food circulation, fomentation material, and the like.

In most cases, such superabsorbent polymer is being widely used in the field of hygienic goods such as a diaper or sanitary pad, etc., and for such use, it is required to exhibit high absorption power to moisture, and the like, and the absorbed moisture should not escape even under external pressure, thus exhibiting excellent absorption performance under pressure.

In addition, the superabsorbent polymer should diffuse urine, and the like as wide as possible, even under pressure by the weight of a user, when included in hygienic products such as a diaper. Thereby, the superabsorbent polymer particles included in the whole area of the absorption layer of a hygienic product may be utilized to further improve absorption performance and absorption speed of the hygienic product. And, due to the diffusion property under pressure, rewet phenomenon wherein a part of urine, and the like absorbed in the superabsorbent polymer exudes again may be inhibited, and thus, leakage inhibition property of a diaper may be improved.

Previously, there had been attempts to improve urine diffusion property by changing the design of hygienic products such as a diaper. For example, there had been attempts to improve urine diffusion property, by introducing ADL (Acquisition Distribution Layer) in hygienic products or applying an absorption channel.

However, diffusion property improvement by design change of hygienic product itself was not sufficient. Furthermore, with the recent thinning of hygienic products and relative increase in superabsorbent polymer content in hygienic products, diffusion property improvement by design change of hygienic product itself reached the limit, and there is an increasing demand for improvement in diffusion under pressure of superabsorbent polymer itself.

Due to such a technical demand, there is an increasing demand for the development of superabsorbent polymer that has more improved permeability under pressure, which is directly related to the diffusion under pressure, and thus, can further improve rewet property and leakage inhibition property of hygienic products such as a diaper, and the like.

DETAILED DESCRIPTION OF THE INVENTION

Technical Problem

The present invention provides superabsorbent polymer that not only has excellent basic absorption performance, but also exhibits more improved permeability under pressure, and thus, can further improve rewet property of hygienic products such as a diaper, and the like, and a method for preparing the same.

Technical Solution

There is provided superabsorbent polymer comprising
base resin powder comprising first crosslinked polymer of water soluble ethylenically unsaturated monomers having acid groups of which at least a part are neutralized; and
a surface crosslink layer on the base resin powder, comprising second crosslinked polymer formed by additional crosslinking of the first crosslinked polymer by a surface crosslinking agent,
wherein the surface crosslinking agent comprises a polymer type first surface crosslinking agent having number average molecular weight of 300 or more, and having plural hydroxy groups or epoxy groups.

There is also provided a method for preparing superabsorbent polymer comprising the steps of:
conducting crosslinking polymerization of water soluble ethylenically unsaturated monomers having acid groups of which at least a part are neutralized, in the presence of an internal crosslinking agent, to form hydrogel polymer comprising first crosslinked polymer;
drying, grinding and sieving the hydrogel polymer to form base resin powder; and
heat treating the base resin powder in the presence of a surface crosslinking agent, to conduct surface crosslinking,
wherein the surface crosslinking agent comprises a polymer type first surface crosslinking agent having number average molecular weight of 300 or more, and having plural hydroxy groups or epoxy groups.

Hereinafter, superabsorbent polymer and a method for preparing the same according to specific embodiments of the invention will be explained in detail. However, they are presented only as the illustrations of the invention, the scope of the right of the invention is not limited thereby, and it would be obvious to one of ordinary knowledge in the art that various modifications to the embodiments can be made within the scope of the right of the invention.

And, unless otherwise described throughout the specification, the term "comprise" or "contain" refers to comprising any constructional element (or constructional component) without specific limitations, and it cannot be interpreted as excluding the addition of other constructional elements (or constructional components).

According to one embodiment of the invention, there is provided superabsorbent polymer comprising base resin powder comprising first crosslinked polymer of water soluble ethylenically unsaturated monomers having acid groups of which at least a part are neutralized; and a surface crosslink layer on the base resin powder, comprising second crosslinked polymer formed by additional crosslinking of the first crosslinked polymer by a surface crosslinking agent, wherein the surface crosslinking agent comprises a polymer type first surface crosslinking agent having number average molecular weight of 300 or more, and having plural hydroxy groups or epoxy groups.

The superabsorbent polymer of one embodiment comprises a polymer type surface first crosslinking agent having number average molecular weight of 300 or more, and having crosslinkable functional groups, so as to form a surface crosslink layer.

Since the polymer type first surface crosslinking agent comprises polymer chains having molecular weight above a certain level, it is difficult to penetrate deeply into base resin powder during surface crosslinking, and mostly causes crosslinking around the surface of base resin powder to form a crosslink structure. Thus, superabsorbent polymer formed by the method may have increased crosslinking density around the surface, without significantly increasing the total amount of the surface crosslinking agent used during the preparation process, and furthermore, it may comprise high molecular weight polymer structures derived from the first surface crosslinking agent at higher rate around the surface.

Thus, since the superabsorbent polymer according to one embodiment is harder around the surface, it may exhibit improved permeability under pressure than known before, and thus, may further improve rewet property or leakage inhibition property of hygienic products.

And simultaneously, in order to realize such hard surface property, the superabsorbent polymer does not need to use excessively high content of surface crosslinking agents, and thus, it can maintain appropriate internal crosslinking density, and excellent absorption performance such as centrifuge retention capacity, and the like.

Thus, the superabsorbent polymer of one embodiment can not only maintain excellent basic absorption performance, but also exhibit more improved permeability under pressure, thereby further improving rewet property of hygienic products such as a diaper, and the like.

Hereinafter, superabsorbent polymer and a method for preparing the same according to embodiments will be explained in detail.

As used herein, 'superabsorbent polymer' refers to superabsorbent polymer comprising base resin powder comprising first crosslinked polymer of water soluble ethylenically unsaturated monomers having acid groups of which at least a part are neutralized; and a surface crosslink layer on the base resin powder, comprising second crosslinked polymer formed by additional crosslinking of the first crosslinked polymer by a surface crosslinking agent.

The water soluble ethylenically unsaturated monomers may be any monomers commonly used for the preparation of superabsorbent polymer. As non-limiting examples, the water soluble ethylenically unsaturated monomer may be a compound represented by the following Chemical Formula 1.

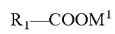         [Chemical Formula 1]

In the Chemical Formula 1, $R_1$ is a C2-5 alkyl group comprising an unsaturated bond, $M^1$ is a hydrogen atom, a monovalent or divalent metal, an ammonium group or an organic amine salt.

Preferably, the acrylic acid-based monomers may be one or more selected from the group consisting of acrylic acid, methacrylic acid, and monovalent metal salts, divalent metal salts, ammonium salts and organic amine salts of these acids. In case acrylic acid or a salt thereof is used as the water soluble ethylenically unsaturated monomer, superabsorbent polymer having improved absorption property may be obtained. In addition, as the monomers, one or more selected from the group consisting of anionic monomers such as maleic anhydride, fumaric acid, crotonic acid, itaconic acid, 2-acryloyl ethanesulfonic acid, 2-methacryloyl ethanesulfonic acid, 2-(meth)acryloyl propanesulfonic acid, or 2-(meth)acrylamid-2-methyl propanesulfonic acid, or salts thereof; hydrophilic group-containing monomers such as (meth)acrylamide, N-substituted (meth)acrylate, 2-hydroxyethyl (meth)acrylate, 2-hydroxypropyl (meth)acrylate, methoxy polyethyleneglycol (meth)acrylate or polyethylene glycol (meth)acrylate; and amino group-containing unsaturated monomers such as (N,N)-dimethylaminoethyl (meth)acrylate or (N,N)-dimethylaminopropyl (meth)acrylamide, and quaternized products thereof may be used.

Wherein, the water soluble ethylenically unsaturated monomers may have acid groups, and at least a part of the acid groups may be neutralized. Preferably, monomers that are partially neutralized with alkali substance such as sodium hydroxide, potassium hydroxide, ammonium hydroxide, etc. may be used.

Wherein, the neutralization degree of monomers may be 40 to 95 mol %, or 40 to 80 mol %, or 45 to 75 mol %. Although the range of the neutralization degree may vary according to the final properties, if the neutralization degree is too high, neutralized monomers may be precipitated, thus rendering smooth progression of polymerization difficult, and to the contrary, if the neutralization degree is too low, absorption power of the polymer may be significantly lowered, and the polymer may exhibit rubber-like property, which is difficult to handle.

In the superabsorbent polymer of one embodiment, the 'first crosslinked polymer' means material formed by crosslinking polymerization of water soluble ethylenically unsaturated monomers in the presence of an internal crosslinking agent, and the 'base resin powder' means material comprising the first crosslinked polymer. And, the 'second crosslinked polymer' means material formed by additional crosslinking of the first crosslinked polymer by a surface crosslinking agent, and a surface crosslink layer comprising the same is formed on the base resin powder.

In the superabsorbent polymer of one embodiment, the first crosslinked polymer included in the base resin powder may be a polymer formed by crosslinking polymerization of the monomers in the presence of one or more internal crosslinking agents selected from the group consisting of C8-12 bis(meth)acrylamide, C2-10 polyol poly(meth)acrylate and C2-10 polyol poly(meth)allylether. As specific examples of the internal crosslinking agent, although not specifically limited, trimethylolpropane tri(meth)acrylate, ethyleneglycol di(meth)acrylate, polyethyleneglycol di(meth)acrylate, propyleneglycol di(meth)acrylate, polypropyleneglycol di(meth)acrylate, butanedioldi(meth)acrylate, butyleneglycoldi(meth)acrylate, diethyleneglycol di(meth)acrylate, hexanediol di(meth)acrylate, triethyleneglycol di(meth)acrylate, tripropyleneglycol di(meth)acrylate, tetraethyleneglycol di(meth)acrylate, dipentaerythritol pentaacrylate, glycerin tri(meth)acrylate, and pentaerythritol tetraacrylate, and the like may be mentioned, and besides, various internal crosslinking agents known to be used for the preparation of superabsorbent polymer may be used without specific limitations.

Meanwhile, in the superabsorbent polymer of one embodiment, using a polymer type first surface crosslinking agent having number average molecular weight of 300 or more and having functional groups capable of reacting with the carboxy groups on the surface of the base resin powder such as plural hydroxy groups or epoxy groups, the surface crosslink layer is formed.

As the first surface crosslinking agent, any polymers having number average molecular weight of 300 or more, or 300 to 30000, or 350 to 15000, and having functional groups capable of reacting with the carboxy groups, specifically, plural hydroxy groups or epoxy groups, may be used without specific limitations. As specific example of the polymer type crosslinking agent, polymer having the above explained number average molecular weight, and selected from the group consisting of polyethylene glycol-based polymer, polypropylene glycol-based polymer, polyol polyglycidyl ether-based polymer such as polyalkyleneglycol diglycidyl ether, and polyvinyl alcohol-based polymer, may be mentioned.

If a surface crosslinking agent having molecular weight or number average molecular weight below the above range is used as the first surface crosslinking agent (for example, two kinds of surface crosslinking agents which are not in the form of polymer are used), permeability under pressure of superabsorbent polymer may be deteriorated, and thus, rewet property or leakage inhibition property of hygienic products may not be sufficient.

And, the superabsorbent polymer of one embodiment may use a second surface crosslinking agent which is not in the form of polymer and has molecular weight less than 300, in addition to the first surface crosslinking agent, and thus, comprise crosslink structure derived therefrom together.

As the second surface crosslinking agent, any surface crosslinking agent in the form of single molecule, previously used in the preparation of superabsorbent polymer, may be used without specific limitations. For example, the surface crosslinking agent may include one or more polyols selected from the group consisting of ethylene glycol, propylene glycol, 1,3-propanediol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol and glycerol; one or more alkylene carbonate compounds selected from the group consisting of ethylene carbonate and propylene carbonate; epoxy compounds such as alkylene glycol diglycidyl ether, and the like; oxazoline compounds such as oxazolidinone, and the like; or cyclic urea compounds. Preferably, the alkylene carbonate compound may be appropriately used.

Since the superabsorbent polymer of one embodiment uses plural kinds of surface crosslinking agents, particularly, the polymer type first surface crosslinking agent and the second surface crosslinking agent together, it may increase crosslinking density around the surface of superabsorbent polymer, without increasing the total amount/content of the surface crosslinking agents. Thus, since the superabsorbent polymer of one embodiment is harder around the surface, it may exhibit more improved permeability under pressure than known before, and thus, may further improve rewet property or leakage inhibition property of hygienic products.

In order to exhibit such properties, in the superabsorbent polymer of one embodiment, the crosslink structure derived from the first surface crosslinking agent may exist at the highest rate on the outermost surface of the surface crosslink layer, and the existence rate may decrease as the depth of the surface crosslink layer is deeper.

The above explained first surface crosslinking agent: second surface crosslinking agent may be included at a weight ratio of 3:1 to 1:3, or 2.5:1 to 1:2.5, or 2:1 to 1:2. Thereby, the surface of the superabsorbent polymer may become harder, and thus, not only the rewet property or leakage inhibition property of hygienic products may be further improved, but also the absorption performance of the superabsorbent polymer may be maintained excellent.

Meanwhile, the superabsorbent polymer of one embodiment may further comprise various multivalent metal salts including aluminum salts such as aluminum sulfate, so as to further improve permeability, and the like. Such multivalent metal salts may be included in the surface crosslink layer of the finally prepared superabsorbent polymer.

Meanwhile, the superabsorbent polymer of one embodiment may have particle diameter of 150 to 850 µm. More specifically, at least 95 wt % of the base resin powder and superabsorbent polymer comprising the same may have particle diameter of 150 to 850 µm, 50 wt % or more may have particle diameter of 300 to 600 µm, and less than 3 wt % may be fine powder having particle diameter less than 150 µm.

And, the superabsorbent polymer of one embodiment may exhibit more improved permeability under pressure, while maintaining excellent absorption performance such as centrifuge retention capacity.

Specifically, the excellent absorption performance of the superabsorbent polymer of one embodiment may be defined as centrifuge retention capacity and absorbency under pressure. More specifically, centrifuge retention capacity (CRC) for 30 minutes for a saline solution (0.9 wt % aqueous sodium chloride solution) may be 28 to 43 g/g, or 30 to 40 g/g. Such a centrifuge retention (CRC) range may define excellent absorption performance under no pressure of the superabsorbent polymer of one embodiment.

And, absorbing under pressure (AUP) of 0.7 psi, measured according to EDANA method WSP 242.3-10, may be 15 to 27 g/g, or 20 to 25 g/g. Such a range of absorbing under pressure may define excellent absorption performance under pressure of the superabsorbent polymer of one embodiment.

In addition, improved permeability under pressure of the superabsorbent polymer may be defined by GPUP. The GPUP may be measured as a flow for 5 minutes from the time when the first drop falls, when the superabsorbent polymer is swollen under pressure of 0.3 psi in a saline solution (0.9 wt % aqueous sodium chloride solution) for 1 hour, and then, the saline solution is dropped to the superabsorbent polymer. More specific measurement method will be described in Experimental Examples below.

The superabsorbent polymer of one embodiment may exhibit GPUP of $5 \cdot 10E-13$ $m^2$ or more, or 5 to $30 \cdot 10E-13$ $m^2$, or 7 to $25 \cdot 10E-13$ $m^2$, thus exhibiting excellent permeability under pressure.

Since the superabsorbent polymer of one embodiment exhibits more improved permeability under pressure than known before, it may not only improve rewet property of hygienic products, but also maintain excellent absorption performance.

Meanwhile, the superabsorbent polymer fulfilling all the properties may be prepared by obtaining hydrogel polymer by crosslinking polymerization, and then, drying, grinding and sieving it to form base resin powder, and conducting surface crosslinking in the presence of specific surface crosslinking agents.

According to another embodiment of the invention, there is provided a method for preparing the above explained superabsorbent polymer. The method comprises the steps of: conducting crosslinking polymerization of water soluble ethylenically unsaturated monomers having acid groups of which at least a part are neutralized, in the presence of an internal crosslinking agent, to form hydrogel polymer comprising first crosslinked polymer; drying, grinding and sieving the hydrogel polymer to form base resin powder; and heat treating the base resin powder in the presence of a surface crosslinking agent, to conduct surface crosslinking, wherein the surface crosslinking agent comprises a polymer type first surface crosslinking agent having number average molecular weight of 300 or more, and having plural hydroxy groups or epoxy groups.

Hereinafter, the preparation method will be explained in detail according to each step.

First, the preparation method of another embodiment comprises the step of forming hydrogel polymer by crosslinking polymerization. Specifically, a monomer composition comprising water soluble ethylenically unsaturated monomers and a polymerization initiator is subjected to thermal polymerization or photopolymerization in the presence of an internal crosslinking agent, to form hydrogel polymer.

The water soluble ethylenically unsaturated monomers included in the monomer composition are as explained above.

And, in the monomer composition, a polymerization initiator commonly used for the preparation of superabsorbent polymer may be included. As non-limiting example, as the polymerization initiator, a thermal polymerization initiator or a photopolymerization initiator may be used according to a polymerization method. However, even in case photopolymerization is progressed, since a certain amount of heat is generated by UV irradiation, etc., and heat is generated to some degree according to the progression of an exothermic polymerization reaction, a thermal polymerization initiator may be additionally included.

As the photopolymerization initiator, one or more selected from the group consisting of benzoin ether, dialkyl acetophenone, hydroxyl alkylketone, phenyl glyoxylate, benzyl dimethyl Ketal, acyl phosphine, and α-aminoketone may be used. Among them, as the acyl phosphine, commercially available lucirin TPO, i.e., 2,4,6-trimethyl-benzoyl-trimethyl phosphine oxide may be used. More various photopolymerization initiators are described in Reinhold Schwalm, "UV Coatings: Basics, Recent Developments and New Application (Elsevier 2007)", page 115, which may be referred to.

And, as the thermal polymerization initiator, at least one selected from the group consisting of a persulfate initiator, an azo initiator, hydrogen peroxide, and ascorbic acid may be used. Specific examples of the persulfate initiator may include sodium persulfate ($Na_2S_2O_8$), potassium persulfate ($K_2S_2O_8$), ammonium persulfate (($NH_4)_2S_2O_8$), etc., and, specific examples of the azo initiator may include 2,2-azobis (2-amidinopropane)dihydrochloride, 2,2-azobis-(N,N-dimethylene)isobutyramidinedihydrochloride, 2-(carbamoylazo)isobutyronitril, 2,2-azobis[2-(2-imidazolin-2-yl)propane]dihydrochloride, 4,4-azobis-(4-cyanovalericacid), etc. More various thermal initiators are described in "Principle of Polymerization (Wiley, 1981)", Odian, page 203, which may be referred to.

The polymerization initiator may be added at the concentration of 0.001 to 1 wt %, based on the monomer composition. Specifically, if the concentration of the polymerization initiator is too low, polymerization speed may become slow, and remaining monomers may be extracted in a large quantity in the final product. To the contrary, if the concentration of the polymerization initiator is too high, polymer chains making up a network may become short, and thus, water soluble content may increase and absorption under pressure may decrease, thereby deteriorating the properties of polymer.

Meanwhile, in the monomer composition, a crosslinking agent (internal crosslinking agent) for improving the properties of polymer formed by polymerization of water soluble ethylenically unsaturated monomers is included. The crosslinking agent is used to internally crosslink hydrogel polymer, and may be used separately from the "surface crosslinking agent" described below.

Particularly, in the preparation method of another embodiment, the above explained internal crosslinking agent, for example, C8-12 bis(meth)acrylamide, C2-10 polyol poly(meth)acrylate or C2-10 polyol poly(meth)allylether, and the like may be used, and thereby, hydrogel polymer with appropriate internal crosslink may be obtained. The kind of internal crosslinking agents is already explained, and thus, additional explanations are omitted.

And, the internal crosslinking agent may be used in the content of 0.4 to 2 parts by weight, or 0.4 to 1.8 parts by weight, based on 100 parts by weight of the monomer composition comprising the internal crosslinking agent and monomers, and the like. Thereby, the internal crosslinking degree of hydrogel polymer and base resin powder may be controlled, and absorption performance and permeability of superabsorbent polymer may be optimized. However, if the content of the internal crosslinking agent is too high, basic absorption performance of superabsorbent polymer may be deteriorated.

Besides, the monomer composition may further comprise additives such as a thickener, a plasticizer, a preservation stabilizer, an antioxidant, etc., as necessary.

And, the monomer composition may be prepared in the form of a solution in which the above explained raw materials including monomers, polymerization initiators, internal crosslinking agent, and the like are dissolved in a solvent.

Wherein, the solvent that can be used is not limited in terms of its construction as long as it can dissolve the above explained raw materials. For example, as the solvent, water, ethanol, ethyleneglycol, diethyleneglycol, triethyleneglycol, 1,4-butanediol, propyleneglycol, ethyleneglycol monobutyl ether, propyleneglycol monomethyl ether, propyleneglycol monomethyl ether acetate, methylethylketone, acetone, methylamylketone, cyclohexanone, cyclopentanone, diethyleneglycol monomethyl ether, diethyleneglycol ethyl ether, toluene, xylene, butyrolactone, carbitol, methylcellosolve acetate and N,N-dimethylacetamide, or a mixture thereof may be used.

And, the formation of hydrogel polymer through the polymerization of the monomer composition may be conducted by a common polymerization method, and the process is not specifically limited. As non-limiting examples, the polymerization method is largely classified into thermal polymerization and photopolymerization according to an energy source. Commonly, thermal polymerization may be progressed in a reactor equipped with a stirring axis such as a kneader, and photopolymerization may be progressed in a reactor equipped with a movable conveyer belt.

For example, hydrogel polymer may be obtained by introducing the above described monomer composition into a reactor equipped with a stirring axis such as a kneader, and supplying hot air or heating the reactor to progress thermal polymerization. Wherein, the hydrogel polymer discharged to the outlet of the reactor may in the size of a few centimeters to a few millimeters according to the shape of the stirring axis equipped in the reactor. Specifically, the size of obtained hydrogel polymer may vary according to the concentration of the introduced monomer composition and the introduction speed, etc., and commonly, hydrogel polymer with a (weight average) particle diameter of 2 to 50 mm may be obtained.

And, in case photopolymerization of the monomer composition is progressed in a reactor equipped with a movable conveyer belt, hydrogel polymer in the form of a sheet may be obtained. Wherein, the thickness of the sheet may vary according to the concentration of the introduced monomer composition and the introduction speed or introduction amount, but preferably, it is controlled to 0.5 to 10 cm, so as to enable uniform polymerization of the whole sheet and secure production speed.

Wherein, the moisture content of hydrogel polymer obtained by such a method may be 40 to 80 wt %. Throughout the specification, the "moisture content" is the content of moisture occupied based on the total weight of hydrogel polymer, and it means a value obtained by subtracting the weight of polymer of a dry state from the weight of hydrogel polymer. Specifically, it is defined as a value calculated by measuring the weight loss according to moisture evaporation in the polymer while raising the temperature of polymer through infrared heating to dry. At this time, the drying condition is set up such that the temperature is raised from room temperature to 180° C. and then maintained at 180° C., and the total drying time is 40 minutes including a temperature raising step of 5 minutes.

Next, the obtained hydrogel polymer is dried. Wherein, a step of coarsely grinding the hydrogel polymer may be further conducted before drying the hydrogel polymer so as to increase drying efficiency.

Wherein, grinders that can be used in the coarse grinding is not limited in terms of the constructions, but specifically, one selected from the group consisting of a vertical pulverizer, a turbo cutter, a turbo grinder, a rotary cutter mill, a cutter mill, a disc mill, a shred crusher, a crusher, a chopper, a disc cutter may be used, but the grinder is not limited thereto.

Through the coarse grinding step, the particle diameter of the hydrogel polymer may be controlled to about 2 to about 10 mm. Grinding to a particle diameter less than 2 mm would not be technically easy due to the high moisture content of hydrogel polymer, and cause caking between ground particles. Meanwhile, if grinding to a particle diameter greater than 10 mm, the effect for increasing the efficiency in the subsequent drying step may be insignificant.

The hydrogel polymer coarsely ground as explained above, or hydrogel polymer immediately after polymerization that has not been subjected to the coarse grinding step is dried. Here, the drying temperature may be 150 to 250° C. If the drying temperature is less than 150° C., a drying time may become excessively long, and the properties of the finally formed superabsorbent polymer may be deteriorated, and if the drying temperature is greater than 250° C., only the surface of polymer may be dried to generate fine powders in the subsequent grinding process, and the properties of the finally formed superabsorbent polymer may be deteriorated. Thus, it is preferable that the drying is progressed at a temperature of 150 to 200° C., more preferably 170 to 195° C.

Meanwhile, a drying time may be about 20 to about 90 minutes, considering process efficiency, and the like, but is not limited thereto.

And, the drying method is not limited in terms of the construction as long as it is commonly used as a drying process of hydrogel polymer. Specifically, the drying step may be progressed by hot wind supply, infrared ray irradiation, ultrahigh frequency wave irradiation, or UV irradiation, etc. The polymer dried by such a method may exhibit a moisture content of about 0.1 to about 10 wt %.

Next, the dried polymer obtained through the drying step is ground.

The particle diameter of the polymer powder obtained after the grinding step may be 150 μm to 850 μm. As a grinder for grinding to such a particle diameter, specifically, a pin mill, a hammer mill, a screw mill, a roll mill, a disc mill, or a jog mill, etc. may be used, but the grinder is not limited thereto.

And, in order to manage the properties of the superabsorbent polymer powders finally productized after the grinding step, the polymer powders obtained after grinding may be subjected to a separate process of sieving according to the particle diameter. Preferably, polymer having diameter of 150 to 850 μm may be sieved, and thereby, only polymer powders having such particle diameters may be subjected to surface crosslinking and productized. More specifically, sieved base resin powders may have particle diameters of 150 to 850 μm, and may comprise 50 wt % or more of particles having particle diameters of 300 to 600 μm.

Meanwhile, after passing through the above explained sieving process to prepare base resin powder, the base resin powder may be surface crosslinked while heat treated, in the presence of a surface crosslinking agent, to form superabsorbent polymer particles. The surface crosslinking induces a crosslinking reaction on the surface of the base resin powder in the presence of a surface crosslinking agent, and through the surface crosslinking, a surface crosslink layer may be formed on the surface of the base resin powder.

More specifically, in the preparation method of another embodiment, a polymer type first surface crosslinking agent having number average molecular weight of 300 or more is used, and a second surface crosslinking agent that is not in the form of polymer may be selectively used together. The kinds of the surface crosslinking agents are already explained, and thus, additional explanations are omitted.

In the surface crosslinking process using the surface crosslinking agents, the contents of the surface crosslinking agents may be appropriately controlled according to the kind of the crosslinking agents or reaction conditions, and the like, and preferably, the first and second surface crosslinking agents may be used respectively in the content of 0.1 to 2.0 part by weight, or 0.3 to 1.5 parts by weight, or 0.5 to 1.0 parts by weight, based on 100 parts by weight of the base resin powder.

If the content of the surface crosslinking agent is too low, surface modification may not properly achieved, thus deteriorating the properties of the final polymer. Particularly, if the content of the polymer type first surface crosslinking agent is low, permeability under pressure of superabsorbent polymer may not be sufficient. To the contrary, if an excessive amount of surface crosslinking agent is used, due to excessive surface crosslinking reactions, basic absorption performance of polymer may be deteriorated on the contrary.

Meanwhile, the surface crosslinking agents are added to the base resin powder in the form of a surface crosslinking solution comprising the same, and the method of adding the surface crosslinking solution is not specifically limited. For example, the surface crosslinking solution and base resin powder may be put in a reactor and mixed, the surface crosslinking solution may be sprayed to base resin powder, or the base resin powder and surface crosslinking solution may be continuously fed to a continuously operated mixer and mixed.

And, the surface crosslinking solution may further comprise water and/or hydrophilic organic solvents as a medium. Thereby, the surface crosslinking agents, and the like may be uniformly dispersed on the base resin powder. Wherein, the contents of water and hydrophilic organic solvents added, based on 100 parts by weight of the base resin powder, may be controlled so as to induce uniform dissolution/dispersion of the surface crosslinking agents, prevent the agglomeration of the base resin powder, and optimize the surface penetration depth of the surface crosslinking agent.

The base resin powder to which the surface crosslinking solution is added may be heat treated at a temperature of 140° C. to 250° C., or 140° C. to 220° C., or 170° C. to 210° C. for more than 30 minutes, thus progressing surface crosslinking. More specifically, the surface crosslinking may be progressed by heat treating at the above explained maximum reaction temperature, for 30 to 80 minutes, or 40 to 70 minutes.

By fulfilling such surface crosslinking process conditions (particularly, temperature rise condition and reaction condition at the maximum reaction temperature), superabsorbent polymer appropriately fulfilling excellent properties such as excellent permeability under pressure may be prepared.

A temperature rise means for surface crosslinking is not specifically limited. A heating medium may be fed, or a heat source may be directly fed to heat. Wherein, the kind of heating medium that can be used may include temperature increased fluid such as steam, hot air, hot oil, and the like, but is not limited thereto, and may be appropriately selected considering temperature rise speed and targeted temperature. Meanwhile, as the heat source that is directly fed, electric heating, gas heating may be mentioned, but is not limited thereto.

The superabsorbent polymer obtained according to the above explained preparation method may widely diffuse urine, and the like absorbed in hygienic products, while maintaining absorption performance such as centrifuge retention capacity and permeability, thereby significantly improving rewet property of hygienic products.

Advantageous Effects

The superabsorbent polymer according to the invention may not only maintain excellent basic absorption performance, but also exhibit more improved permeability under pressure, thus enabling rapid and wide diffusion of urine, and the like absorbed in hygienic products along the surface of the superabsorbent polymer particles. As the result, the superabsorbent polymer of the invention may improve rewet property and leakage inhibition property of hygienic products.

DETAILED DESCRIPTION OF THE EMBODIMENTS

Hereinafter, preferable examples are presented for better understanding of the invention. However, these examples are presented only as the illustrations of the invention, and the invention is not limited thereby.

Example 1

Based on 100 parts by weight of acrylic acid monomers, 40.6 parts by weight of caustic soda (NaOH), and 131.2 parts by weight of water were mixed, and to the mixture, 0.12 parts by weight of a thermal polymerization initiator of sodium persulfate, 0.008 parts by weight of a photopolymerization initiator of diphenyl(2,4,6-trimethylbenzoyl)-phosphine oxide, and 0.22 parts by weight of an internal crosslinking agent of polyethylene glycol diacrylate were added, thus preparing a monomer composition.

While the monomer composition was flowed at the flow rate of 243 kg/hr on the polymerization belt of a continuous belt polymerization reactor, of which internal temperature is maintained at 80° C., and on top of which a UV irradiation device having an intensity of 10 mW with a mercury UV lamp light source is installed, UV was irradiated for 1 minute, and a polymerization reaction was progressed for additional 2 minutes without a light source.

A hydrogel type polymerization sheet emerging after the polymerization was finished was primarily cut using a Shredder type cutter, and then, coarsely ground through a meat chopper. Thereafter, it was dried at 180° C. for 30 minutes through a hot air dryer, and then, ground using a rotary mixer and sieved to 150 μm to 850 μm, thus preparing base polymer powders.

The prepared base resin powders were mixed at a particle size rate of 10/70/19/1, and 200 parts by weight was prepared. And, 100 parts by weight of the base resin powders were uniformly mixed with 5.4 parts by weight of water, 0.6 parts by weight of ethylene carbonate, 0.5 parts by weight of polymer type surface crosslinking agent of polyethylene glycol diglycidylether having number average molecular weight of 500, 0.2 parts by weight of propylene glycol, and 0.4 parts by weight of aluminum sulfate 18 hydrate, and then, while raising the temperature to 180° C. and heat treating for more than 50 minutes, a surface crosslinking reaction was progressed. After completing the surface treatment, superabsorbent polymer having particle diameter of 850 μm or less was obtained using a sieve.

Example 2

Superabsorbent polymer of Example 2 was obtained by the same method as Example 1, except that polyethyleneglycol diglycidyl ether having number average molecular weight of 380 was used as the polymer type surface crosslinking agent.

Example 3

Superabsorbent polymer of Example 3 was obtained by the same method as Example 1, except that polyvinyl alcohol having number average molecular weight of 10,000 was used as the polymer type surface crosslinking agent.

Example 4

Superabsorbent polymer of Example 4 was obtained by the same method as Example 1, except that ethylene carbonate was not used, and the content of the polymer type surface crosslinking agent was changed to 1.1 parts by weight.

Comparative Example 1

Superabsorbent polymer of Comparative Example 1 was obtained by the same method as Example 1, except that the polymer type surface crosslinking agent was not used.

Comparative Example 2

Superabsorbent polymer of Comparative Example 2 was obtained by the same method as Example 1, except that the polymer type surface crosslinking agent was not used, and the content of ethylene carbonate was changed to 1.1 parts by weight.

Comparative Example 3

Superabsorbent polymer of Comparative Example 3 was obtained by the same method as Example 1, except that ethylene glycol diglycidyl ether having molecular weight of about 174 was used instead of the polymer type surface crosslinking agent.

Comparative Example 4

Superabsorbent polymer of Comparative Example 4 was obtained by the same method as Example 1, except that glycerol triglycidyl ether having molecular weight of 260 was used instead of the polymer type surface crosslinking agent.

Experimental Example

The properties of each superabsorbent polymer prepared in Examples and Comparative Examples were measured and evaluated as follows.

(1) Evaluation of Particle Diameter

The particle diameters of base resin powder and superabsorbent polymer of Examples and Comparative Examples were measured according to EDANA (European Disposables and Nonwovens Association) standard EDANA WSP 220.3.

(2) Centrifuge Retention Capacity (CRC)

Centrifugal retention capacity (CRC) by absorption rate under no load was measured according to European Disposables and Nonwovens Association (EDANA) Standard EDANA WSP 241.3. $W_0$(g, about 0.2 g) of the superabsorbent polymer was uniformly put in an envelope made of non-woven fabric and sealed, and then, soaked in a saline solution (0.9 wt % sodium chloride aqueous solution) at room temperature. After 30 minutes, the envelope was drained at 250G for 3 minutes using a centrifuge, and then, the weight $W_2$(g) of the envelope was measured. And, the same operation was conducted without using superabsorbent polymer, and then, the weight $W_1$(g) at that time was measured. Using the obtained weights, CRC (g/g) was calculated according to the following Calculation Formula 1, thus confirming centrifugal retention capacity.

$$CRC(g/g) = \{[W_2(g) - W_1(g) - W_0(g)]/W_0(g)\} \quad \text{[Calculation Formula 1]}$$

(3) Absorbing Under Pressure (AUP)

For each superabsorbent polymer of Examples and Comparative Examples, absorbency under pressure (AUP) was measured according to European Disposables and Nonwovens Association standard EDANA WSP 242.3-10.

First, on the bottom of a plastic cylinder having an inner diameter of 60 mm, a 400 mesh wire netting made of stainless was installed. Under 23±2° C. temperature and 45% humidity conditions, $W_0$(g) (0.9 g) of each polymer obtained in Examples and Comparative Examples was uniformly sprayed on the wire netting, and a piston having an outer diameter slightly smaller than 60 mm and capable of further giving 4.83 kPa (0.7 psi) load was installed thereon so that there was no gap with the inner wall of the cylinder and the up and down movement was not hindered. At this time, the weight $W_3$(g) of the device was measured.

Inside a petri dish having a diameter of 150 mm, a glass filter having a diameter of 125 mm and a thickness of 5 mm was laid, and a saline solution consisting of 0.9 wt % sodium chloride was put to the same level with the upper side of the glass filter. On the glass filter, the measuring device was laid, and the liquid was absorbed under pressure for 1 hour. After 1 hour, the measuring device was lifted, and the weight $W_4$(g) was measured.

Using each obtained weight, AUP (g/g) was calculated according to the following Calculation Formula.

$$AUP(g/g) = [W_4(g) - W_3(g)]/W_0(g) \quad \text{[Calculation Formula 2]}$$

(4) GPUP

Each superabsorbent polymer of Examples and Comparative Examples was swollen under pressure of 0.3 psi, in a saline solution (0.9 wt % aqueous sodium chloride solution) for 1 hour, and then, the saline solution was dropped to the superabsorbent polymer, and GPUP was measured as a flow for 5 minutes from the time when the first drop falls. Specific measurement method/conditions were as follows.

First, on the bottom of a plastic cylinder having an inner diameter of 60 mm, a 400 mesh wire netting made of stainless was installed. And, a piston having an outer diameter slightly smaller than 60 mm and capable of further giving 2.1 kPa (0.3 psi) load was installed thereon so that there was no gap with the inner wall of the cylinder and the up and down movement was not hindered, and the height (t0) was measured. In the cylinder, superabsorbent polymer (about 1.8±0.05 g) was uniformly applied and the piston was raised, and then, inside a petri dish having a diameter of 200 mm, a glass filter having a diameter of 90 mm and a thickness of 5 mm was laid, and a saline solution consisting of 0.9 wt % sodium chloride was put to the level 5 mm higher than the upper side of the glass filter, and the superabsorbent polymer was absorbed/swollen under load for 1 hour. Thereafter, a saline solution consisting of 0.9 wt % sodium chloride was dropped, and the weight of the saline solution passing through for 5 minutes from the time when the first drop passed through the swollen superabsorbent polymer gel ($F_g$), was measured. After 5 minutes of saline solution passing time, the height of the measuring device (t1) was measured. From the measurement results, GPUP was calculated according to the following Calculation Formulas 3 and 4:

$$K(\cdot 10E\text{-}7 \ cm^3 s/g) = (Fg*t/\rho*A*P) \quad \text{[Calculation Formula 3]}$$

$F_g$=weight of saline solution passing through gel per unit time (g/s)
t(cm)=thickness of superabsorbent polymer gel (t1−t0)/10
$\rho$=density of saline solution (~1 g/cm$^3$)
A=area of cylinder, 28.27 cm$^2$
P=hydrostatic pressure, 4920 dyn/cm$^2$ $$GPUP(\cdot 10E\text{-}13 \ m^2) = (K*\eta*10/10000)*1000000 \quad \text{[Calculation Formula 4]}$$

$\eta$=viscosity of saline solution (~0.0009xx [Pa s])

The properties of Examples 1 to 4 and Comparative Examples 1 to 4 measured by the above methods were summarized in the following Table 1.

TABLE 1

| Unit | CRC g/g | AUP g/g | GPUP ·10E−13 m$^2$ |
|---|---|---|---|
| Example 1 | 35 | 24 | 26 |
| Example 2 | 35 | 24 | 24 |
| Example 3 | 35 | 24 | 23 |
| Example 4 | 35 | 20 | 20 |
| Comparative Example 1 | 35 | 24 | 15 |
| Comparative Example 2 | 33 | 22 | 18 |
| Comparative Example 3 | 35 | 22 | 16 |
| Comparative Example 4 | 35 | 21 | 17 |

Referring to Table 1, it was confirmed that Examples 1 to 4 not only exhibit basic absorption performances (CRC, AUP) equivalent to or more excellent than Comparative Examples 1 to 4, but also have excellent GPUP compared to Comparative Examples, and thus, can widely diffuse urine, and the like.

The invention claimed is:

1. A superabsorbent polymer comprising:
a base resin powder comprising a first crosslinked polymer of water soluble ethylenically unsaturated monomers having acid groups of which at least a part are neutralized; and
a surface crosslink layer on the base resin powder, comprising a second crosslinked polymer formed by additional crosslinking of the first crosslinked polymer by a surface crosslinking agent,
wherein the surface crosslinking agent comprises a polymer first surface crosslinking agent having a number average molecular weight of 300 or more comprising: polyethylene glycol polyglycidyl ether polymer or polyvinyl alcohol polymer,
wherein the surface crosslinking agent further comprises a second surface crosslinking agent having a molecular weight less than 300, comprising:
a polyol comprising propylene glycol;
an alkylene carbonate comprising ethylene carbonate,
wherein the first surface crosslinking agent: the second surface crosslinking agent are included at the weight ratio of 2.5:1 to 1:2.5.

2. The superabsorbent polymer according to claim 1, wherein a crosslink structure derived from the first surface crosslinking agent exists at a highest rate on the outermost surface of the surface crosslink layer, and an existence rate decreases as a depth of surface crosslink layer is deeper.

3. The superabsorbent polymer according to claim 1, further comprising multivalent metal salts on the surface crosslink layer.

4. The superabsorbent polymer according to claim 1, wherein a centrifuge retention capacity (CRC) for 30 minutes for a saline solution (0.9 wt % aqueous sodium chloride solution) is 28 to 43 g/g, and
an absorbency under pressure (AUP) of 0.7 psi, measured according to EDANA method WSP 242.3-10, is 15 to 27 g/g.

5. The superabsorbent polymer according to claim 1, wherein a GPUP is 5.10E−13 m$^2$ or more, said GPUP being measured based on a flow for 5 minutes from a time when a first drop falls, when the superabsorbent polymer is swollen under pressure of 0.3 psi in a saline solution (0.9 wt % aqueous sodium chloride solution) for 1 hour, and then, the saline solution is dropped on to the superabsorbent polymer.

6. The superabsorbent polymer according to claim 1, wherein the polymer first crosslinking agent further comprises one or more of a polyethylene glycol-based polymer or a polypropylene glycol-based polymer.

7. The superabsorbent polymer according to claim 1, wherein the second surface crosslinking agent further comprises one or more polyols selected from the group consisting of ethylene glycol, 1,3-propanediol, 1,4-butanediol, 1,6-butanediol, 1,2-hexanediol, 1,3-hexanediol, 2-methyl-1,3-propanediol, 2,5-hexanediol, 2-methyl-1,3-pentanediol, 2,5-hexanediol, 2-methyl-1,3-pentanediol, 2-methyl-2,4-pentanediol, tripropylene glycol and glycerol; an alkylene carbonate comprising propylene carbonate; epoxy compounds of alkylene glycol diglycidyl ether; oxazoline compounds or cyclic urea compound.

8. A method for preparing superabsorbent polymer according to claim 1 comprising
conducting crosslinking polymerization of water soluble ethylenically unsaturated monomers having acid groups of which at least a part are neutralized, in the presence of an internal crosslinking agent, to form a hydrogel polymer comprising a first crosslinked polymer;
drying, grinding and sieving the hydrogel polymer to form a base resin powder; and
heat treating the base resin powder in the presence of a surface crosslinking agent, to conduct surface crosslinking,
wherein the surface crosslinking agent comprises a polymer first surface crosslinking agent having a number average molecular weight of 300 or more, and having plural hydroxy groups or epoxy groups.

9. The method for preparing superabsorbent polymer according to claim 8, wherein the surface crosslinking agent further comprises a second surface crosslinking agent having molecular weight less than 300, comprising:
one or more polyols selected from the group consisting of ethylene glycol, propylene glycol, 1,3-propanediol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol and glycerol;
one or more alkylene carbonate compounds selected from the group consisting of ethylene carbonate and propylene carbonate;
epoxy compounds of alkylene glycol diglycidyl ether;
oxazoline compounds; or
cyclic urea compounds.

10. The method for preparing superabsorbent polymer according to claim 8, wherein the base resin powder has a particle diameter of 150 to 850 μm, and the base resin powder is ground and sieved such that it comprises 50 wt % or more of particles having particle diameters of 300 to 600 μm.

11. The method for preparing superabsorbent polymer according to claim 9, wherein the first and second surface crosslinking agents are respectively used in a content of 0.1 to 2.0 parts by weight, based on 100 parts by weight of the base resin powder.

12. The method for preparing superabsorbent polymer according to claim 8, wherein the surface crosslinking is progressed by heat treating and reacting at a reaction temperature of 140° C. to 250° C. for 30 minutes or more.

* * * * *